United States Patent [19]

Abernathy et al.

[11] 4,442,048

[45] Apr. 10, 1984

[54] METHOD AND APPARATUS FOR CONTROLLING THE FORMATION OF POLYMER ACCUMULATIONS DURING DISTILLATION OF A VINYLAROMATIC MONOMER

[75] Inventors: Marshall Abernathy, Big Spring, Tex.; Darrell E. Bailey, Prairieville, La.

[73] Assignee: Cosden Technology, Inc., Dallas, Tex.

[21] Appl. No.: 364,479

[22] Filed: Apr. 1, 1982

Related U.S. Application Data

[62] Division of Ser. No. 230,617, Feb. 2, 1981, Pat. No. 4,374,000.

[51] Int. Cl.³ .............................................. B01D 3/22
[52] U.S. Cl. ............................... 261/114 R; 202/158; 203/9; 261/114 TC
[58] Field of Search .......... 203/9; 261/114 R, 114 JP, 261/114 TC; 202/158

[56] References Cited

U.S. PATENT DOCUMENTS

| 3,448,015 | 6/1969 | Rogers | 203/9 |
| 3,717,553 | 2/1973 | Otsuki et al. | 203/9 |

Primary Examiner—Frank Sever
Attorney, Agent, or Firm—Schwartz, Jeffery, Schwaab, Mack, Blumenthal & Koch

[57] ABSTRACT

A method for controlling the formation of polymer accumulations in a distillation column comprising accumulating liquid phase material containing a polymerization inhibitor in a seal pan; providing the seal pan with liquid-pervious weep hole means through the bottom of the pan and allowing a controlled quantity of polymerization inhibitor-containing liquid phase material to seep through the weep hole means to the underside of the seal pan; and apparatus useful for practicing the disclosed method.

15 Claims, 4 Drawing Figures

4,442,048

METHOD AND APPARATUS FOR CONTROLLING THE FORMATION OF POLYMER ACCUMULATIONS DURING DISTILLATION OF A VINYLAROMATIC MONOMER

This is a division of application Ser. No. 230,617, filed Feb. 2, 1981. Now U.S. Pat. No. 4,374,000.

BACKGROUND OF THE INVENTION

This invention relates to a process and apparatus for producing readily polymerizable vinylaromatic compounds. More particularly, this invention relates to a process and apparatus for inhibiting the accumulation of undesired polymeric material on the undersides of the seal pans of a distillation column during distillative purification of vinylaromatic monomers.

Vinylaromatic monomers, such as styrene, alpha-alkylstyrene, vinyltoluene, divinylbenzene and the like, are important for their ability to form useful polymer materials. These compounds are typically prepared by catalytic dehydrogenation of alkylaromatic compounds having corresponding carbon chains. The crude product of the dehydrogenation reaction, however, is a mixture of materials comprising in addition to the desired vinylaromatic monomer, various alkylaromatic compounds as well as oligomers of the desired monomer. These other substances must be separated from the vinylaromatic monomer to obtain a commercially acceptable product.

The usual method for separating a desired vinylaromatic monomer from the dehydrogenation product mixture is to pass the mixture through a distillation train in which lower boiling materials are first separated and then the desired monomer is distilled from the higher boiling materials. Such distillative separations are complicated by the fact that the tendency of the monomer to polymerize increases with increasing temperature. Thus, as the mixture is heated to distill it, the formation of undesired polymer increases and the yield of desired monomer decreases.

Various measures have been utilized to minimize the undesired polymer formation. Vacuum distillation, i.e. distillation at subatomspheric pressures, has been resorted to to reduce the temperature to which the feed mixture must be heated. While this is helpful in reducing the formation of undesired polymeric material, substantial amounts of polymer still are formed.

Polymerization inhibitors have also been added to the feed mixture. Known inhibitors further reduce the formation of undesired polymer, but still are not totally effective. Moreover, such inhibitors may be expensive and contribute substantially to the production costs of the vinylaromatic monomer.

A particular problem arises in areas in the distillation apparatus where there is little vapor motion, such as adjacent the undersides of the seal pans. Monomer vapors condense against the cool undersides of the pans and form droplets of liquid monomer which may polymerize and solidify before they grow large enough to drop down into the underlying tray. Masses of unwanted polymeric material thus build up in the distillation apparatus. Liquid phase active inhibitors do not prevent such deposits because the condensing vapors do not carry these inhibitors with them. Even the use of vapor phase active inhibitors is not totally effective in supressing the formation of such deposits because the lack of vapor motion under the seal pans restricts the mixing of the inhibitor with the condensing vapors.

The continuing accumulation of undesired polymeric material thus requires that the distillation apparatus used to purify vinylaromatic monomers be periodically shut down and cleaned of the fouling polymer. As the polymer is typically a dense hard material, considerable difficulty may be encountered in cleaning the distillation apparatus. The need for periodic cleaning increases operating costs, and capital costs are also increased because additional distillation capacity must be constructed in order to compensate for the down time of the distillation apparatus.

Despite the efforts of the prior art, there remains a substantial need for improved methods and apparatus for inhibiting the formation of undesired polymeric residues in distillation apparatus used to purify vinylaromatic monomers.

OBJECTS OF THE INVENTION

Accordingly, it is an object of the present invention to provide an improved method and apparatus for inhibiting the formation of polymerized vinylaromatic compounds during distillative purification of a crude vinylaromatic monomer feed.

Another object of the present invention is to provide a method and apparatus for inhibiting the formation of polymerized vinylaromatic compounds which will not increase the need for expensive chemical inhibitors.

A further object of the present invention is to provide a method and apparatus for inhibiting the formation of polymerized vinylaromatic compounds which will permit distillation systems used to purify vinylaromatic monomers to be run for longer periods before shutdown for cleaning becomes necessary.

It is also an object of the present invention to provide method and apparatus for inhibiting the formation of polymerized vinylaromatic compounds in the areas under the seal pans of the distillation apparatus where there is little vapor motion.

Yet another object of the present invention is to provide a method and apparatus for inhibiting the formation of polymerized vinylaromatic compounds during distillative purification of a vinylaromatic monomer which will increase the yield of monomer.

An additional object of the present invention is to provide a method and apparatus for purifying a vinylaromatic monomer which will decrease the formation of undesired soluble and insoluble polymer by-products.

A still further object of the present invention is to provide a method for distilling a vinylaromatic monomer which inhibits fouling of the distillation column and an apparatus for distilling a vinylaromatic monomer which is less prone to fouling.

It is also an object of the present invention to provide a method and apparatus for producing substantially pure vinylaromatic monomer which is more economical than prior art methods.

SUMMARY OF THE INVENTION

These and other objects of the invention are achieved by providing a method for controlling the formation of polymer accumulations on the undersides of the seal pans in a distillation column used for distillative purification of a vinylaromatic monomer comprising accumulating liquid phase material containing an effective polymerization inhibiting concentration of polymerization inhibitor in the seal pans, providing liquid pervious weep hole means through the seal pans, and allowing a controlled quantity of polymerization inhibitor-containing liquid phase material from the seal pans to seep through the weep hole means to the undersides of the seal pans.

The objects of the invention are further achieved by providing apparatus for controlling the formation of polymer accumulations on the undersides of the seal pans in a distillation column used for distillative purification of a vinylaromatic monomer comprising at least one distillation column containing a series of gas/liquid contact trays having seal pans associated therewith for providing a liquid seal between successive trays in the series; said seal pans being provided with liquid pervious weep hole means through the bottoms thereof.

BRIEF DESCRIPTION OF THE DRAWINGS

The invention will be further explained with reference to the accompanying drawings wherein.

DETAILED DESCRIPTION OF PREFERRED EMBODIMENTS

Figure 1:
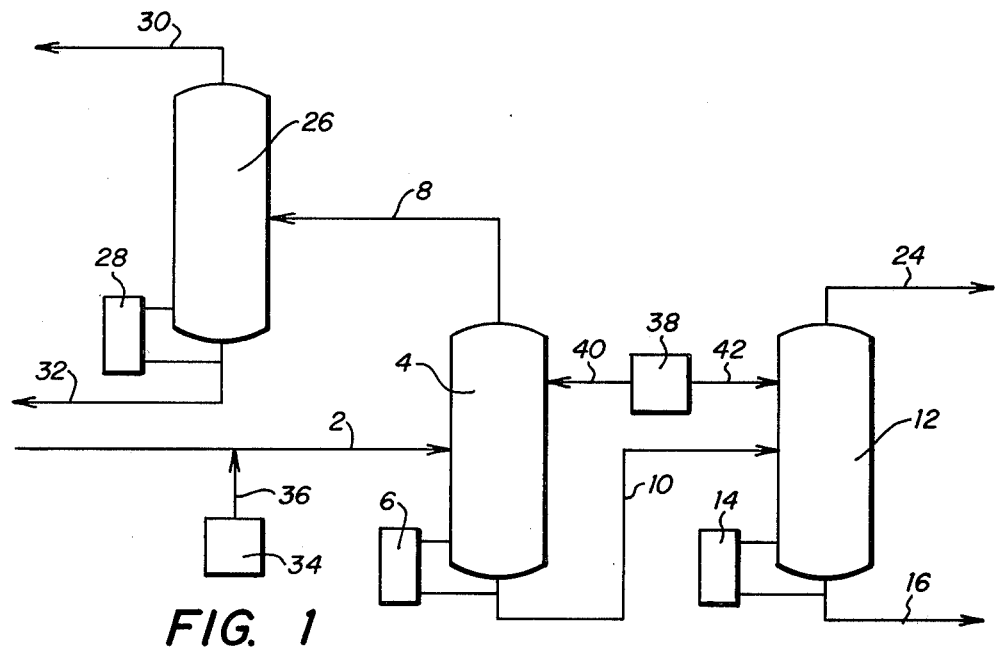
FIG. 1 is a schematic representation of a distillation system for purifying a crude vinylaromatic monomer.

Referring now to the drawings, FIG. 1 shows schematically a distillation system for purifying crude vinylaromatic monomer. The illustrated system will be described in conjunction with the distillation of vinyltoluene, but it is understood that the distillation system and the invention are useful for purifying other vinylaromatic monomers such as styrene, alpha-methylstyrene, divinylbenzene and the like. It is considered within the skill of the art to adjust the operating parameters as necessary to adapt the system to other vinylaromatic monomers.

A crude vinyltoluene feed recovered from the dehydrogenation of ethyltoluene is condensed and introduced through line 2 into the intermediate portion of a recycle distillation column 4. Recycle column 4 is a conventional multi-tray distillation column containing a series of suitable vapor/liquid contact devices such as bubble cap trays, perforated trays, valve trays, etc. Either single path or parallel path columns may be utilized although the parallel distillation path design is preferred. Typically, the number of trays in recycle column 4 will range between 40 and 100. Preferably, at least about 72 trays are provided in the recycle column in order to facilitate proper separation of the constituents of the crude vinyltoluene feed mixture.

The recycle column is typically operated at temperatures ranging between about 65 and about 138 degrees C. and at absolute pressures ranging from about 0.013 to about 0.26 atmospheres (10 to 200 mm Hg). Preferably distillation temperatures in the recycle column lie between about 90 and about 115 degrees C. and the pressure is maintained between about 0.04 and about 0.15 atmospheres. A reboiler 6 is associated with distillation column 4 to provide the heat necessary to maintain distillation conditions in the column. Reboiler temperatures are maintained between about 90 and about 120 degrees C. by controlling the reboiler pressure between about 0.04 and about 0.50 atmospheres (30 to 400 mm Hg). A recycle overhead fraction comprising principally a mixture of lower boiling alkylaromatic compounds such as ethyltoluene, xylene and toluene, is withdrawn from the top of recycle column 4 through line 8.

The recycle bottoms fraction, comprising principally vinyltoluene admixed with higher boiling materials such as vinyltoluene oligomers, is withdrawn from the bottom of recycle column 4 through line 10 and introduced into the intermediate portion of finish distillation column 12. Finish column 12 is a multitray distillation column similar in design to recycle column 4. Finish column 12 typically contains between about 15 and about 30 trays. The finish column is operated at a temperature lying in the range from about 70 to about 100 degrees C. and at an absolute pressure lying in the range from about 0.01 to about 0.06 atmospheres. A reboiler 14 is associated with finish column 12 to provide the heat necessary to maintain appropriate distillation conditions in the finish column.

The finish column bottoms fraction, comprising principally tarry residues admixed with some residual vinyltoluene monomer, is withdrawn from the bottom of finish column 12 through line 16. The finish column overhead fraction withdrawn from column 12 through line 24 comprises substantially pure vinyltoluene.

In the illustrated distillation scheme, the recycle overhead fraction withdrawn from recycle column 4 through line 8 is introduced into an alkylbenzene distillation column 26. Alkylbenzene column 26 is also a conventional distillation column similar in design to recycle column 4, except that the alkylbenzene column typically contains 40 or fewer trays. The alkylbenzene column is operated at a temperature from about 125 to about 190 degrees C. and at an absolute pressure from about 0.9 to about 1.7 atmospheres. A reboiler 28 is associated with alkylbenzene column 26 to provide the heat necessary to maintain appropriate distillation conditions in the distillation column. An overhead fraction comprising low boiling aromatics such as xylene, toluene and/or benzene is withdrawn from the top of alkylbenzene column 26 through line 30. This fraction may be used as a solvent, or it may be conveyed to further reaction steps such as isomerization or alkylation. The alkylbenzene column bottoms fraction comprising principally the vinyltoluene precursor, ethyltoluene, is withdrawn from the bottom of alkylbenzene column 26 through line 32 and returned to the dehydrogenation reactor to produce additional vinyltoluene.

Generally, polymerization inhibitors are introduced into the vinyl aromatic monomer during the distillation. Preferred inhibitors include nitrated phenolic compounds such as dinitro-o-cresol, dinitro-p-cresol, m-nitro-p-cresol, dinitrophenol, N-nitroso-diphenylamine, 4-halo-3,5-dinitrotoluene, 3-nitro-2,5-cresotic acid and the like. Sulfur may also be used as an inhibitor, but its use is not preferred because the resulting sulfur-containing tarry residues have little economic value and are very difficult to dispose of. Mixtures of inhibitors may be used. A particularly preferred inhibitor comprises a mixture of N-nitroso-diphenylamine (NDPA) which is active primarily in the vapor phase and dinitro-p-cresol (DNPC) which is active primarily in the liquid phase.

The inhibitors may be introduced in any desired manner. Inhibitor from a source of inhibitor 34 may be introduced through line 36 into the crude vinyltoluene feed in line 2 prior to introduction of the feed into recycle column 4. Inhibitor from a source 38 may be introduced directly into recycle column 4 and/or finish column 12 through lines 40 and 42, respectively. It is also possible to add inhibitor to the reboilers.

The amount of inhibitor required depends upon the specific inhibitor used, but generally lies between about 50 and about 3000 ppm with respect to the vinyltoluene. Higher amounts may be utilized, but ordinarily little benefit is gained from the additional expenditure. In most cases, the inhibitor concentration will lie between about 200 and about 1000 ppm with respect to the vinyltoluene. Since the inhibitors are generally stable, the tarry residues recovered from the finish column usually contain appreciable amounts of inhibitor. The amount of fresh inhibitor required to be introduced into the distillation system may optionally be reduced by recycling a portion of the inhibitor-containing tarry residues back to recycle column 4 either by mixing the residue with the crude feed entering through line 2 or by introducing the residue directly into the recycle column.

Figure 2:
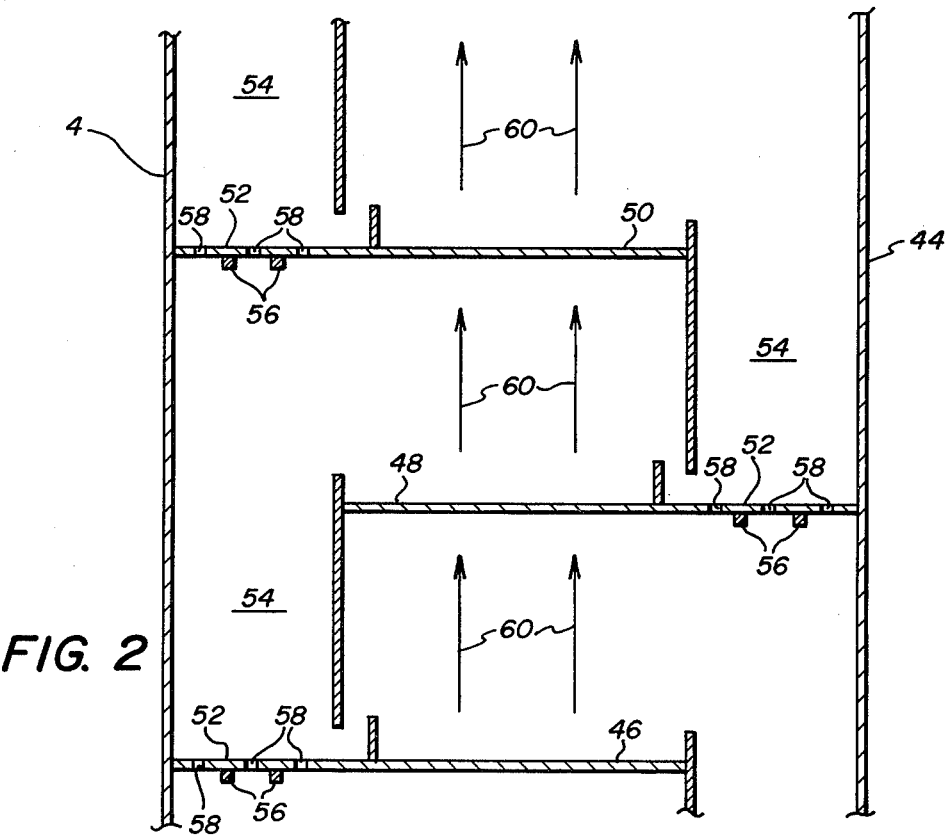
FIG. 2 is a schematic sectional representation of a portion of a distillation column for purifying vinylaromatic monomer.

FIG. 2 is a schematic partial sectional view of recycle distillation column 4 showing a portion of the distillation column wall 44 and three of the internal gas/liquid contact trays 46, 48 and 50, respectively. A seal pan 52 is shown under the downcomer area 54 of each tray. Supports underlying the seal pans are designated by reference numeral 56. Liquid phase material collects at the bottom of downcomer 54 in each downcomer seal pan 52. A series of weep holes 58 are provided through the bottoms of downcomer seal pans 52. Typically the weep hole means take the form of a series of small circular apertures, but it is understood that it is not essential that the weep holes be round. The size of the weep holes is critical. If the holes are too small, liquid phase material will not flow down through the holes. The holes will merely fill with liquid which will remain in the holes until it polymerizes and plugs the holes. If the holes are too large, then liquid will flow too rapidly through the holes and too much liquid will bypass the active area of the tray, thereby adversely affecting the distillation efficiency of the column. Similar disadvantages accrue if there are too many weep holes through the bottom of the tray. If the weep holes are too large or if there are too many weep holes, it is even possible that the liquid seal on the tray may be lost. Another disadvantage of holes which are too large is the fact that vapor from the underlying tray will pass through the holes and cause foaming in the downcomer above the seal pan. This can result in liquid flooding of the column and reduced column capacity.

The weep holes should be sufficiently large that liquid phase material will seep steadily through the holes to the underside of the seal pan, but they should not be so large that the liquid can run through in a steady stream. It has been found that the weep holes should be not less that about 2 mm in diameter nor more than about 10 mm in diameter. Preferably the weep holes will be between about 4 mm and about 8 mm in diameter. The spacing between adjacent weep holes should be not less than about 50 mm nor more than about 150 mm. Desirably the distance between adjacent weep holes will be from about 4 to about 25 times the diameter of the holes. It is particularly desirable that weep holes be positioned adjacent the column wall and next to the supports underlying the seal pans as these are areas where polymer accumulations are especially likely to form.

In the operation of the distillation column, vinyltoluene vapors designated by arrows 60 rise from each tray through the column toward the tray above. Some of the vapors contact the cool bottoms of seal pans 52 where they condense. Eventually, the droplets of condensed vapor will become large enough to fall back onto the underlying trays. However, problems occur if the condensed vinyltoluene polymerizes before the droplets become large enough to fall back to the underlying tray. The polymerized vinyltoluene will gradually build up on the undersides of the seal pans until it is necessary to take the distillation column out of service for cleaning.

During normal operation of the distillation column, liquid phase material accumulates in the seal pans at the bottoms of the downcomers. This liquid phase material will contain some of the polymerization inhibitor introduced into the distillation column which prevents the liquid phase material in the seal pans from polymerizing.

In the invention, a controlled amount of the liquid phase material from the seal pans is allowed to seep through weep holes 58 to the undersides of the seal pans. The amount of liquid which seeps through the weep holes is controlled by the number and size of the holes. Some polymerization inhibitor passes through the weep holes with the seeping liquid phase material. This inhibitor material mixes with the condensing vinyltoluene on the underside of the seal pan and serves to inhibit polymerization of the condensing vinyltoluene. Moreover, the seeping liquid phase material assists in washing the condensed vinyltoluene from the bottom of the seal pan back down to the underlying tray. Accumulation of a mass of polymerized vinyltoluene on the undersides of the seal pans is thus prevented.

It is not necessary that every seal pan in the distillation column be provided with weep hole means. If desired, only selected trays under which polymer accumulations are most likely to form may be provided with weep hole means.

Further details of the invention will be apparent from a consideration of the following examples.

EXAMPLE 1

A series of approximately 1.5 mm (1/16th inch) diameter weep holes was provided through the bottom of the seal pan associated with tray 29 of a 72 tray recycle distillation column used for distillative purification of vinyltoluene. The column was then placed in service in the distillation of vinyltoluene. Dinitro-o-cresol at a concentration of 500 ppm with respect to the vinyltoluene was used as a polymerization inhibitor. Column temperatures were maintained at 105±7 degrees C. After 6 weeks, the column was taken out of service. The seal pan provided with weep holes and the seal pan of the next higher tray were examined for polymer accumulations. It was found that the weep holes were plugged with polymeric material and that the polymer accumulation under the seal pan of tray 29 was only slightly less than that under the seal pan of tray 30. This test shows that the weep holes must be greater in size than 1.5 mm.

EXAMPLE 2

Figure 3:
FIG. 3 is a photograph of the underside of a recycle distillation column seal pan provided with weep hole means according to the invention at the end of a vinyltoluene production run.
Figure 4:
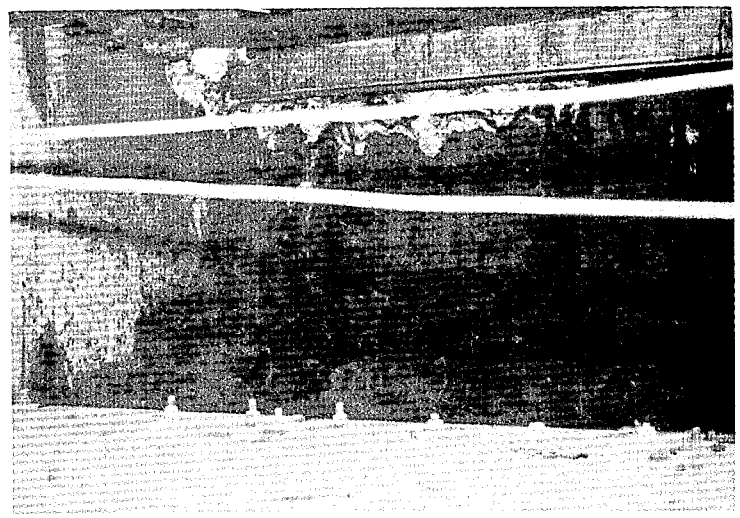
FIG. 4 is a similar photograph of the underside of an adjacent seal pan not provided with weep hole means according to the invention.

The distillation column of Example 1 was cleaned, and the weep holes in tray 29 were enlarged to a diameter of 6.3 mm (¼th inch). The distillation column was then placed back in service. After 60 days operation, the column was again taken out of service and the undersides of the trays were inspected. As can be from FIG. 3, only a very slight polymer accumulation was found under the seal pan of tray 29 which had been provided with the weep holes of the invention. In contrast thereto, a substantial polymer accumulation was again found under the seal pan of tray 30 as can be seen from FIG. 4. This example shows that the weep holes of the invention, when properly sized, are effective in preventing the formation of undesired polymer accumulations on the undersides of the seal pans.

The foregoing description and examples have been set forth merely for purposes of exemplification and are not intended as limiting. Since modifications of the disclosed embodiments within the scope and spirit of the invention may occur to persons skilled in the art, the scope of the invention is to be limited solely by the scope of the appended claims:

We claim:

1. Apparatus for controlling the formation of polymer accumulations on the underside of a seal pan underneath a downcomer in a downcommer-equipped distillation column used for distillative purification of a vinylaromatic monomer, said apparatus comprising:
   at least one downcomer-equipped distillation column comprising a series of gas/liquid contact trays, at least some of said trays having associated therewith a downcomer and a seal pan positioned underneath said downcomer for providing a liquid seal between successive trays in said series; and
   means, provided in at least one seal pan and including liquid pervious weep holes spaced and dimensioned therethrough, for allowing a liquid phase material containing an effective polymerization inhibiting concentration of polymerization inhibitor accumulated on said seal pan to seep through said weep holes to the underside of said seal pan.

2. Apparatus according to claim 1 comprising:
   recycle distillation column means for separating a recycle overhead fraction comprising lower boiling materials from a recycle bottoms fraction comprising vinylaromatic monomer and higher boiling materials;
   means for introducing said crude feed into said recycle distillation column means;
   means for maintaining said recycle distillation column means at an appropriate distillation temperature;
   finish distillation column means for separating a finish overhead fraction of substantially pure vinylaromatic monomer from a finish bottoms fraction containing higher boiling materials;
   means for withdrawing said recycle bottoms fraction from said recycle distillation column means and introducing said recycle bottoms fraction into said finish distillation column means;
   means for maintaining said finish distillation column means at an appropriate distillation temperature; and
   means for collecting said finish overhead fraction of substantially pure vinylaromatic monomer.

3. Apparatus according to claim 2, further comprising:
   alkylbenzene distillation column means for separating an alkylbenzene bottoms fraction comprising the alkylbenzene precursor of said vinylaromatic monomer from an alkylbenzene overhead fraction comprising other lower boiling materials;
   means for withdrawing said recycle overhead fraction from said recycle distillation column and introducing said recycle overhead fraction into said alkylbenzene distillation column means;
   means for maintaining said alkylbenzene distillation column means at an appropriate distillation temperature; and
   means for collecting said alkylbenzene bottoms fraction of vinylaromatic monomer precursor.

4. Apparatus according to claim 2, wherein each said distillation temperature maintaining means comprises a reboiler associated with one of said distillation column means.

5. Apparatus according to claim 2, further comprising means for recovering residual vinylaromatic monomer from said finish bottoms fraction.

6. Apparatus according to claim 1, further comprising means for maintaining said distillation column means at subatmospheric pressure.

7. Apparatus according to claim 1, further comprising means for introducing a polymerization inhibitor into said apparatus.

8. Apparatus according to claim 7, wherein said polymerization inhibitor is introduced in admixture with the crude feed.

9. Apparatus according to claim 7, wherein said polymerization inhibitor is introduced directly to said distillation column means.

10. Apparatus according to claim 7, wherein said polymerization inhibitor is introduced into reboiler means associated with said distillation column means.

11. Apparatus according to claim 1 wherein said weep hole means comprises a plurality of weep holes formed at spaced intervals through the bottom of the seal pan.

12. Apparatus according to claim 11 wherein each weep hole is a circular aperture having a diameter from about 2 to about 10 millimeters.

13. Apparatus according to claim 12 wherein the diameter of each weep hole is from about 4 to about 8 millimeters.

14. Apparatus according to claim 11 wherein the distance between adjacent weep holes is from about 4 to about 25 times the hole diameter.

15. Apparatus according to claim 1 wherein each seal pan in said distillation column is provided with weep hole means.

* * * * *